United States Patent [19]

Ho

[11] Patent Number: 5,701,012

[45] Date of Patent: Dec. 23, 1997

[54] FLUORESCENT BIOLOGICAL PARTICLE DETECTION SYSTEM

[75] Inventor: Jim Yew-Wah Ho, Alberta, Canada

[73] Assignee: Her Majesty the Queen in right of Canada, as represented by the Minister of National Defence, Ottawa, Canada

[21] Appl. No.: 616,475

[22] Filed: Mar. 19, 1996

[51] Int. Cl.$^6$ ................................................ G01N 21/64
[52] U.S. Cl. ............................................. 250/461.2
[58] Field of Search ................................. 250/461.2

[56] References Cited

U.S. PATENT DOCUMENTS 3,566,114  2/1971  Brewer ................................. 250/461.2

FOREIGN PATENT DOCUMENTS 60-260830  12/1985  Japan ................................. 250/461.2

OTHER PUBLICATIONS

William H. Schuette, Darrell V. Lewis, Michael O'Connor, John M. Van Buren, "The design and operation of a dual-beam long–focal–length flurometer for monitouing the oxidative metabolism in vivo." *Medical and Biological Engineering*, vol. 14, No. 2 (mar. 1976) pp. 235–238.

Today Science Tomorrow Defence "Detection of Biological Warfare Agents" pp. 11–18, Jim Ho (1994).

Biotechnol. Prog., 1991, 7:21–27 "Monitoring Cell Concentration and Activity by Multiple Excitation Fuorometry" Li et al.

Suffield Memorandum No. 1421 "Detection of BW Agents: Flow Cytometry Measurement of Bacillus Subtillis (BG) Spore Fluorescence", 1993.

Aerosol Science and Technology 4:89–97 (1985) "Performance of a TSI Aerodynamic Particle Sizer", B. T. Chen, Y.S. Chen, H. C. Yeh.

Practical Flow Cytometry, Second Edition, 1988, p. 84, "How a Flow Ctometer Works", A.R. Liss, Inc. NY, NY by Shapiro et al.

*Primary Examiner*—Constantine Hannaher
*Attorney, Agent, or Firm*—Millen, White, Zelano, & Branigan, P.C.

[57] ABSTRACT

A process and apparatus are provided for detection of viable and potentially hazardous biological particles which may be dispersed in a particulate-containing airstream. The process comprises directing each of the contained particles along a linear path through air, in a sequential manner, and sampling them for determination of their size, whether they are biological and viable, and whether they are present in concentrations greater than background levels. The particle size identifies the particles as respirable or not and the particles are characterized as biological and viable by subjecting each particle in turn, to 340 nm, ultraviolet laser light and looking for the emission of fluorescence which is typically emitted from bacteria or bacterial spore. Fluorescence detected in the 400–540 nm range signals the presence of nicotinamide adenine dinucleotide hydrogen, which is indicative of biological activity or viability.

22 Claims, 9 Drawing Sheets

FLUORESCENT BIOLOGICAL PARTICLE DETECTION SYSTEM

FIELD OF THE INVENTION

The present invention is related to process and apparatus for detecting the presence of biological agents in an airstream, as distinguished from inert particles, by utilizing stimulation and subsequent emission of fluorescence therefrom.

BACKGROUND OF THE INVENTION

There is a recognised need for the detection of undesirable concentrations of potentially harmful airborne bacteria in health care environments, laboratories and in warfare conditions. Processes for the detection of airborne particles, which may contain harmful bacteria such as anthrax (*bacillus anthracis*), typically comprise sizing and characterizing the particles as biological. As bacteria can clump together, the term "particle", used hereinafter, is understood to include inert particles, a single biological entity or biological (typically 1 µm), or an aggregate of these small biologicals (aggregates of about 3-10 µm).

Means for measuring a particle's size include analysis of light scattering, electrical mobility, or particle inertia in an accelerated fluid flow. First, a particle's size is indicative of its potential as a respiratory hazard. Secondly, whether it is biologically hazardous or not requires further determination of the particles composition. Composition or biological characteristics are typically determined using reagent-bases processes (such as the detection of biological iron) or apparatus such as a flow cytometer.

The sizing of particles is readily performed in real-time, but the determination of a particle's composition is generally performed using time consuming, off-line analysis. In events where one or more particles may pose extraordinary risks to humans, such as bacteria and their spores, off-line analysis may provide results too late to make an appropriate and safe response.

The sizing of particles using aerodynamic principles is a conventional technique used widely to obtain high resolution size distributions of particles in the range of 0.5 to 15 µm. As described in the paper *Performance of a TSI Aerodynamic Particle Sizer*, Aerosol Science and Technology, 1985, 4:89-97 by Yeh et al., an air sample containing particles is drawn through a small nozzle that produces an abrupt acceleration in the airstream. The resulting velocity of a particle as it exits the nozzle is dependent upon its inertia and its acceleration in the fast airstream. Therefore, the end velocity of very small particles corresponds nearly with the velocity increase of the air stream, while larger, higher inertia particles resist the acceleration and have a lower end velocity.

Particle end velocities are measured very near the nozzle exit by measuring the time between the particle's sequential interruption of two, closely spaced laser beams just beyond the nozzle's exit. This technique is capable of usefully determining particle sizes in the respirable range of about 0.5 µm to 15 µm.

Applicant has previously employed commercial aerodynamic particle sizing (APS) instruments for rapid detection of "possible" bioaerosol events as disclosed in applicant's 1994 paper *Detection of Biological Warfare Agents*, Today Science Tomorrow Defence, pp.11–18, Ed. C. Boulet, Government of Canada Cat. No. D4-1/175E. As described, these possible events have heretofore only been inferred from the concentrations of particles, in particular size ranges, as being generally consistent with the presence of biologicals. The prevailing disadvantage for applying an APS apparatus for bioaerosol detection lays in its inability to unequivocally distinguish whether the particle is biological or not. Characteristics other than size are needed to distinguish harmful biological particles from inert (ie. mineral) particles.

Conventional liquid flow cytometers have grown in use over the last ten years to become an important tool for the characterization of micro-biological specimens. Flow cytometry is well understood in the art, as described in the paper, *How a flow Cytometer Works*, Practical Flow Cytometry, 1988, p.84, A. R. Liss, Inc. NY, N.Y. by Shapiro et al. Basically, the flow cytometer projects a laser light at a moving stream of particles conveyed in a liquid carrier and uses the resultant light scatter or fluorescence to identify individual particle's characteristics.

In optical instruments, the presence of air interposed between the viewing optics and the particle degrades the viewing quality. Thus, in the flow cytometer, the particles are first prepared by immersion in an optically transparent fluid. Further, in some cases, particles are labelled with a fluorescent tag, such as by tagged monoclonal antibody-antigen reactions. The particle-laden liquid is passed through one or more overlapped laser-light beams. Light which scatters upon contact with the particles is measured and any fluorescence is detected in one or more emission wave bands.

By measuring the forward scatter and applying predetermined criteria, the particle size may be determined. Using the side scatter, a particle's cellular constituents may be determined. Lastly, fluorescence of the particle indicates presence of the expected fluorescent antibody, and more particularly, the antigen it is bound to.

However, fluorescent tagging is not practical for aerosol sampling as one cannot tag all the incoming airborne particles on a real-time basis. Therefore, one must instead investigate the intrinsic characteristics of particles themselves. Further, a flow cytometer requires both prepreparation of the particulate matter in an optically-enhancing liquid carrier, and foreknowledge of the characteristics of the particles of interest (so as to attach an appropriate fluorescent tag). Simply, the flow cytometer does not accept an atmospheric air stream sample for analysis in real-time.

In summary, the APS apparatus is not able to discern between hazardous biological and inert, respirable particles and a flow cytometer is unable to process airborne particles.

In an alternate, reagent-based biological characterization process, continuous use of consumable reagents can become problematical and prohibitively expensive.

Therefore, the present invention is directed towards correcting the deficiencies of the known apparatus so as to enable an operator to perform real time detection of bioaerosol hazards in the respirable size range, and to establish whether they are inert or biological.

SUMMARY OF THE INVENTION

The present invention detects and determines the concentration of biological agents entrained in an airstream and distinguishes them from inert particles. The invention utilizes a combination of aerodynamic particle sizing and fluorescence detection. The invention arises from the discovery that a single particle, comprising one or more biological cells, bacteria or spores, contains sufficient intrinsically fluorescing biological matter (biomolecules) to enable one to establish whether the particle is viable (biologically alive), and thus potentially hazardous. The present invention operates in real-time and avoids pre-preparation of the sample in a liquid carrier.

Basically, the invention is directed towards real-time sampling and identification of biomolecules, present in an airstream (bioaerosols), in the size range 0.5 to 15 μm (the respirable range). This size range covers most airborne bacteria and bacterial clusters. Ideally, the target biomolecule should:

exhibit a high fluorescence intensity so as to produce a strong emission, and thereby be detectable without need for immersion in liquid. This is especially critical for the spore-form of bacteria, which contain very little fluorescing biomolecular constituent; and exhibit a fluorescence emission wavelength which is characteristic of the material of interest so as to distinguish it from other background and irrelevant particle characteristics. Generally, the shorter the excitation wavelength, the higher is the energy required, and the more likely is fluorescence to occur in a wider group of biomolecules, masking the target biomolecule.

Serendipitously, in all living cells there exists a coenzyme or biomolecule, nicotinamide adenine dinucleotide phosphate (NADP). NADP is essential for cellular metabolism as an electron or hydrogen acceptor and is therefore an essential constituent for any biological process to be viable. NADP is the oxidized form of NAD(P)H or NADH (nicotinamide adenine dinucleotide hydrogen), a hydrogen ion bearing biomolecule from the class of flavonoids. NADH is found to comply with the fluorescing criteria described above.

The fluorescence excitation and emission wavelengths of NADH are well separated, which facilitates detection. The excitation wavelength of NADH is centered at 340 nm in the near ultraviolet spectrum, and its fluorescent emission wavelength extends from 400 to 540 nm.

Riboflavin, another flavonoid, has fluorescent wavebands that partially overlap those of NADH, so it may also be detected by a system designed for NADH. The presence of both NADH and riboflavin are characteristic of viable bacteria in an air medium.

The success of the present invention is based on the surprising discovery that individual, clusters or even spore-forms of bacteria, upon excitation with an ultraviolet (UV) laser will demonstrate detectable fluorescence, indicative of NADH. Heretofore, applicant was unaware of research which confirmed the presence of NADH in the nearly inert spore form which could be a major form of hazardous biomolecules.

As a result, in a broad process aspect then, the present invention involves the detection of viable biological particles within a stream of air containing a mixture of biologically viable and biologically inert particles, comprising the steps of:

continuously processing the stream of air so as to direct each particle along a substantially linear path through air in a sequential manner;

contacting each particle with an ultraviolet laser beam having a wavelength suitable to excite biomolecules contained therein and produce fluorescence, preferably 320–360 nm;

detecting fluorescence from the particle, preferably in the wavelength range of 400–560 nm which is indicative of NADH contained in the particle, and establishing its fluorescence intensity;

comparing the intensity of each particle's fluorescence against pre-determined criteria so as to establish whether that particle is a biologically viable particle or is an inert particle; and repeating the fluorescence detection and comparison steps for the next particle in sequence.

Preferably, the significance of the presence of biomolecules in the airstream, and particularly for characterizing them as being hazardous, is better defined by:

establishing the size of the examined particle; and establishing the concentration of biological viable particles which are in the respirable size range.

More preferably, the significance and recognition of the potential hazard of biological particles may be further enhanced by first performing the process on the ambient airstream to obtain background values and subsequently comparing them to the process results on the airstream of interest.

The above process is conveniently implemented in apparatus comprising:

means for directing the particles individually and sequentially along a substantially linear path through air;

a source emitting an ultraviolet laser beam directed to contact each particle moving along its linear path in the air, said beam having a wavelength operative to excite biomolecules contained therein to produce fluorescence;

means for measuring the intensity of the fluorescence emitted from each particle and producing a signal indicative thereof; and means for comparing each particle's fluorescence intensity signal against pre-determined criteria and establishing whether that particle is a biologically viable particle or an inert particle.

In a preferred form, the apparatus further comprises:

means for measuring the size of each particle and producing a signal indicative of the particle's size;

means for storing the fluorescence intensity signal and the corresponding particle size signal for each particle;

means for counting the number of particles and producing signals indicative thereof;

means for processing the stored fluorescence intensity, particle size and particle count signals and establishing the concentration of biologically viable particles as a function of particle size, preferably specifically identifying the concentration of biologically viable particles in the respirable size range.

a ultraviolet (UV) laser source having a wavelength chosen to excite nicotinamide adenine dinucleotide hydrogen (NADH), preferably 320–360 nm, and being directed to intercept each particle;

means for detecting fluorescence emitted from each particle, preferably in the range of 400–560 nm, which is indicative of the presence of NADH in that particle;

means for determining the concentration of respirable sized, fluorescing particles detected in the airstream; and means for comparing the concentration of respirable size, fluorescing particles in the airstream against pre-determined levels so as to distinguish a biologically hazardous event from mere background concentrations.

DETAILED DESCRIPTION OF THE PREFERRED EMBODIMENT

Figure 1:
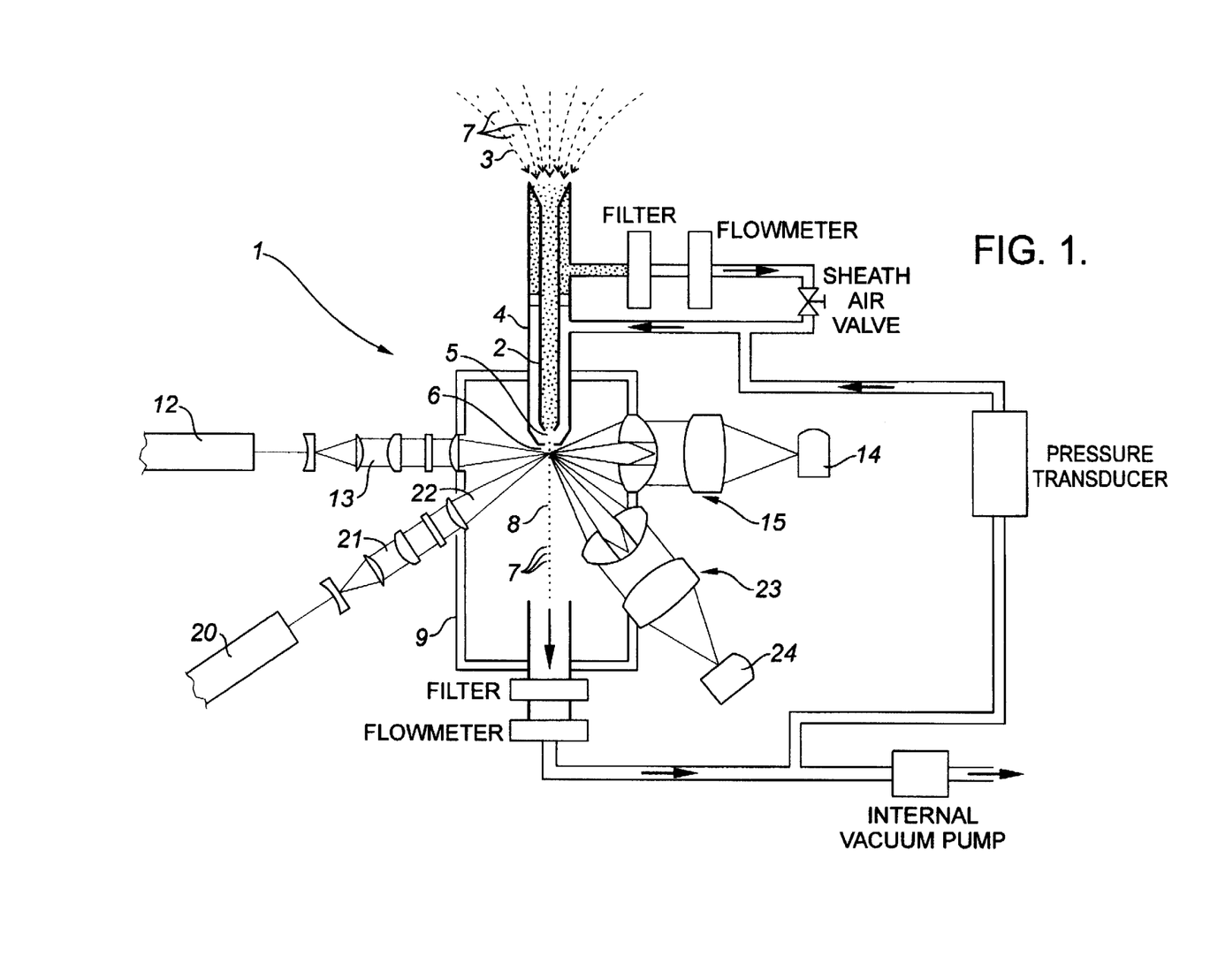
FIG. 1 is a side schematic view of apparatus of one embodiment of the present invention.

As seen in FIG. 1, generally the instrument comprises a nozzle for accelerating an airstream containing particles for discharge past a pair of laser beams. Timing of the particle's flight between laser beams enables determination of the particle's velocity and size. The arrangement of this portion of the apparatus is consistent with a conventional aerodynamic particle sizing (APS) instrument. Next, the particles traverse the beam of a UV laser for fluorescence characterization of the particle as biologically viable or not.

More particularly, the instrument 1 comprises an inner tubular nozzle 2 for discharging 1 liter/rain of the airstream 3. The inner nozzle 2 is concentrically located coaxially within a downwardly oriented outer tubular nozzle 4. The exit 5 of the inner nozzle 2 is adjacent the exit 6 of the outer nozzle 4. About 4 liters/rain of recycled and filtered air is discharged from the outer nozzle's exit 5 for aerodynamically focusing the airstream 3 through the center of the outer nozzle 4.

Figure 2:
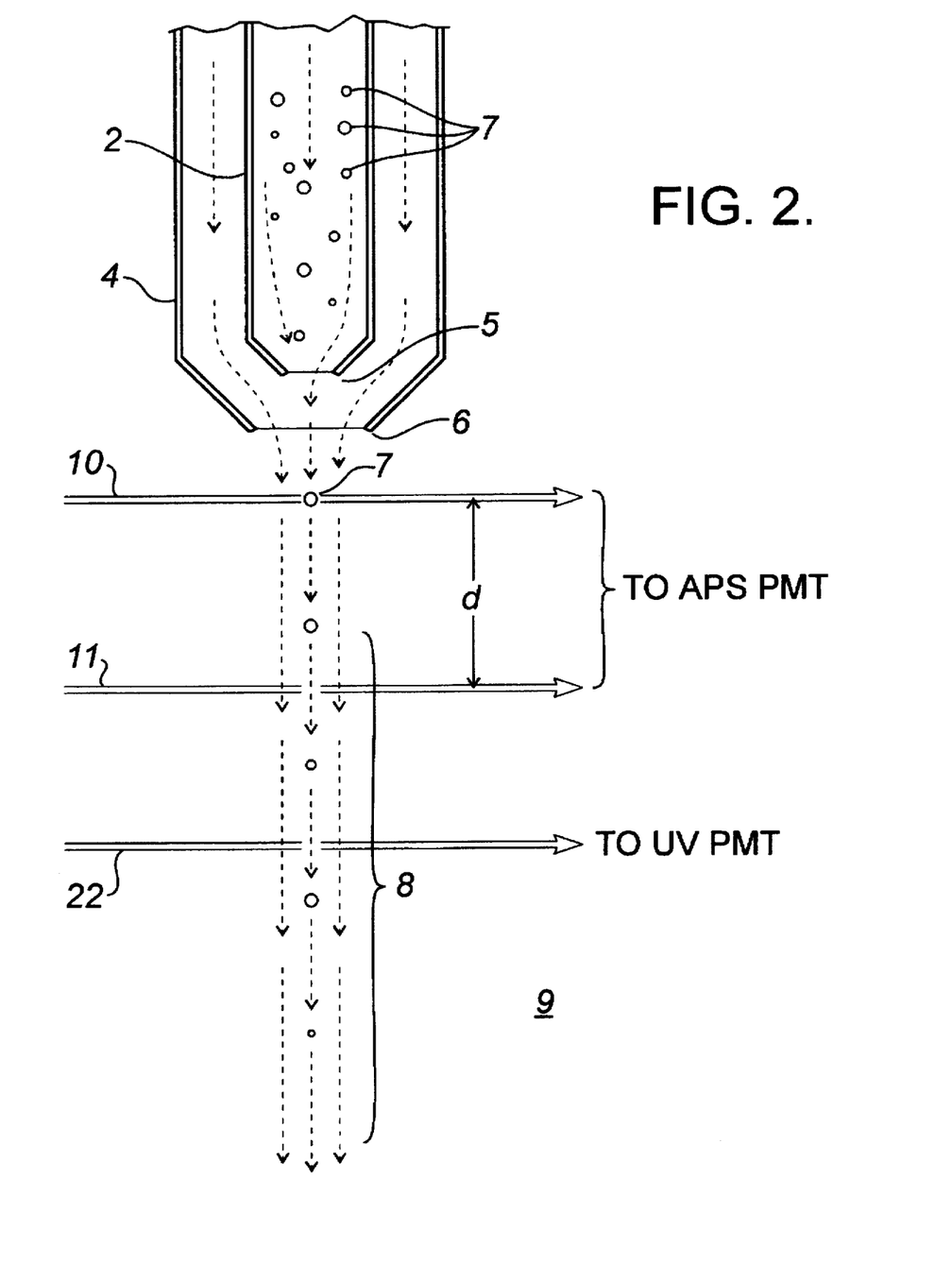
FIG. 2 is a close up view of the nozzles according to FIG. 1, showing the APS and UV laser beams and airborne particles.

As shown in greater detail in FIG. 2, particles 7 exiting the inner nozzle 2 accelerate as they join the greater volumetric air flow of the outer nozzle 4. As the particles 7 in the airstream 3 accelerate, they become physically spaced and exit the outer nozzle in a sequential manner, travelling downwardly along a linear flight path 8 into a recovery chamber 9.

The particles are conveyed in airstream 3, are physically spaced in air, and are discharged into the recovery chamber 9 of air.

Two laser beams 10, 11 are situated adjacent (within about 2 mm) and below the outer nozzle's exit 6. The beams 10,11 lay transverse to and intersect the particle's path 8. The laser beams 10,11 are formed using a red, 633 nm, 2 mW Helium-Neon(He—Ne) laser 12 having its beam shaped with optics 13 and split into the two thin parallel laser beams 10,11. The two beams are closely spaced at a known distance d (typically 2 mm). A particle passing through each one of the laser beams 10,11 will momentarily interrupt that beam. This interruption is detected using a photomultiplier tube ("APS PMT") 14 located on the opposite side of the chamber 9. Each particle's time-of-flight is determined by timing the particle 7 as it crosses first, beam 10 and then, beam 11.

Convergent receiving optics 15 direct the two beams onto the APS PMT 14. The APS PMT is a black, conical light trap located at the focal point of the convergent optics 15, along the axis of the He—Ne beam. Interruption of either beam 10,11 will be detected by the APS PMT 14.

Particle size can be calculated from the timing between beams 10,11. The ultimate particle exit velocity of a particle 7, and thus its time-of-flight, is related primarily to its inertia. The higher the particle's inertia the slower is its exit velocity. A predetermined calibration function enables one to relate the time-of-flight to the particle's size.

Thus far the apparatus described is the same as that taken from a model 3310 aerodynamic particle sizer (APS) available from TSI, Incorporated, St. Paul, Minn.

The apparatus is further modified to accept a 325 nm Helium-Cadmium (He—Cad) laser 20 an focusing optics 21 for directing an ultra-violet spectrum (325 nm) laser beam 22 at the particle's flight path 8 so as to intercept passing particles 7. Receiving optics 23 and a fluorescent PMT 24 are added to receive any fluorescent light, particularly 400–540 nm, which may be emitted from a UV laser intercepted particle 7.

Figure 3:
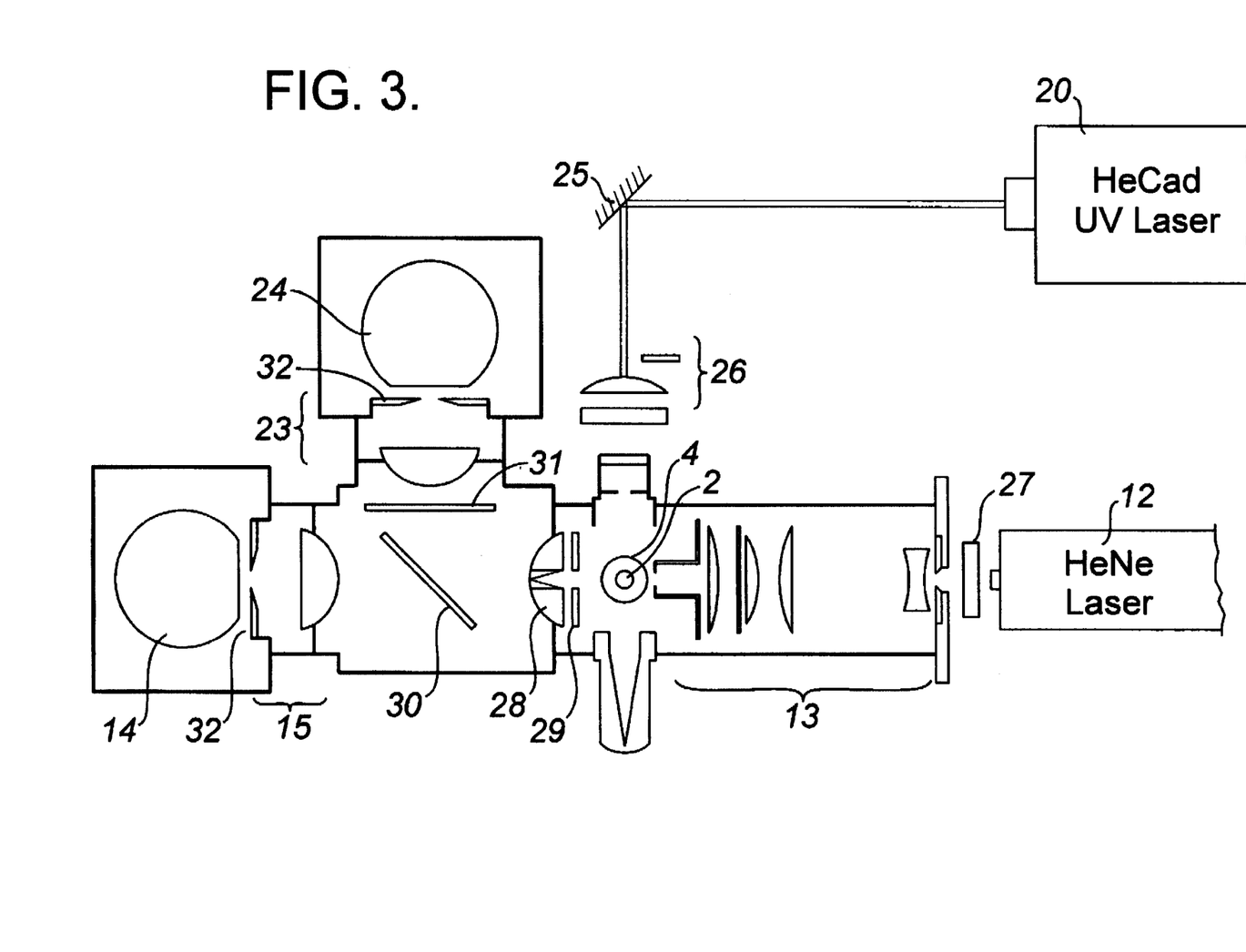
FIG. 3 is a schematic plan view of the apparatus shown in FIG. 1, illustrating the arrangement of the APS and UV lasers.

Having reference to FIG. 3, the He—Ne (APS) laser 12 and He—Cad (UV) laser 20 are oriented a 90 degrees relative to each other. The UV laser 20 is a 30 mw, air-cooled laser available from Liconix, Santa Clara, Calif. This UV laser 20 is approximately 100 cm long. The UV laser, power supply, and APS laser 12 are mounted to a 60 by 150 centimeter optics table and enclosed with a sheet metal cover to give the system a height of about 30 cm. The system weighs about 90 kg and uses 800 watts of electrical power.

The APS laser 12, its optics 13,15 and the UV laser 20 and its optics 21,23 are rigidly mounted to the optics table. A pair of steering mirrors 25 are used to align the UV beam 22. The UV beam 22 is positioned just below the outer nozzle exit 6, just below the APS laser beams 10,11. The UV beam 22 is controlled with a horizontal axis and a vertical axis cylindrical lens 26 at the input. In addition, a 633 nm narrow band transmission optical filter 27 is added at the output of the APS laser 12 to restrict its wavelength to a narrow band and block out any plasma glow, some of which may be within the 420 to 540 nm portion of the fluorescence wavelength detection band of interest.

The receiving optics 15, 23 collect light emitted from particles 7 and direct the light to the respective APS PMT and the fluorescent PMT. The laser light is collected with a high numerical aperture molded asphere primary collection lens 28. Due to the fluorescing borosilicate glass construction, a UV blocking filter (Schott KV399) 29 is located in front of the primary collection lens 28 to block "scattered" ultraviolet light (less than about 400 nm). Visible light emitted from the particles 7 is approximately collimated by the primary collection lens 28 which is followed by a CA-600 dichroic color separation filter 30 mounted at 45 degrees to the APS laser light.

Figure 4:
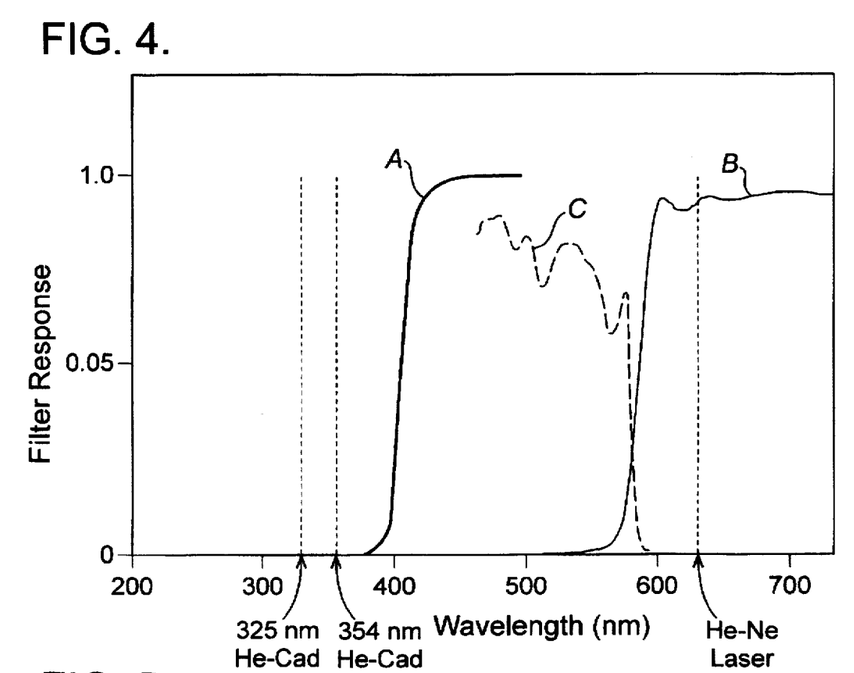
FIG. 4 is a graph depicting the receiving filters response for framing the fluorescent detection wavelengths of interest.

FIG. 4 shows the response of the receiving filters 29,30, 32, (curves A, B and C respectively) for the APS and UV lasers used in the system.

As shown by curve A, the UV blocking filter 29 restricts the light passed to 400 nm and longer. As shown on curve B, the dichroic filter 30 transmits (passes through) any wavelengths longer than about 580 nm to the APS PMT, and reflects shorter wavelengths to the fluorescent PMT. The scattered red He—Ne light is significantly stronger than the blue-green UV fluorescence, so a second optical short pass filter 31, passing about 400–580 nm is placed in front of the fluorescent PMT 24 to further attenuate residual He—Ne light. This is illustrated by curve C. After passing the optical filters 29, 30,31, the scattered He—Ne light and the blue-green florescence are each focused onto the respective PMT's through field stop apertures 32.

Figure 5:
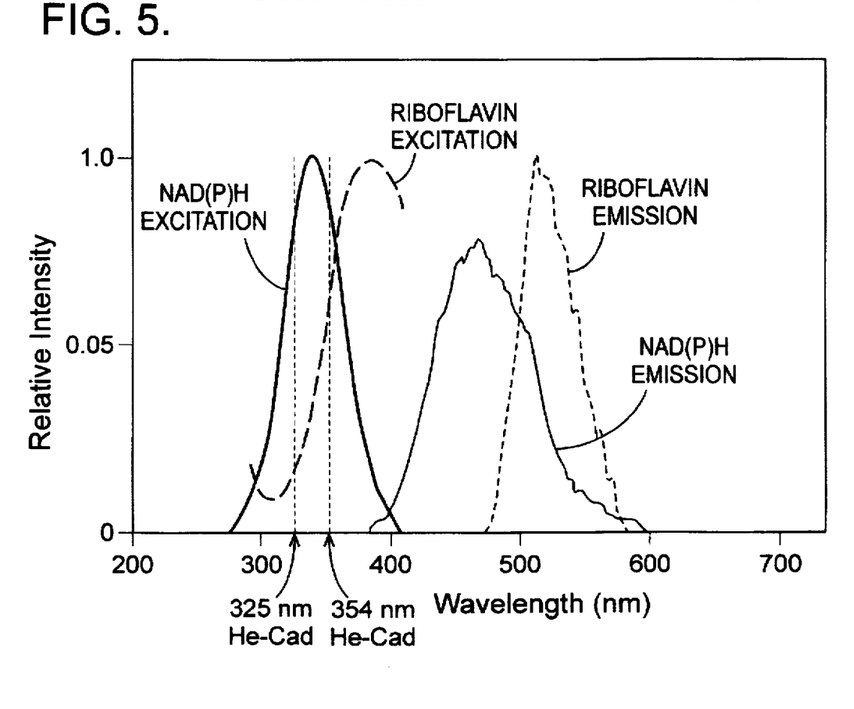
FIG. 5 is a graph depicting the excitation and emission wavelengths for NADH and Riboflavin.

The 400–580 nm region enclosed by curves A, B and C represents the wavelength window for fluorescence signals of interest. This may be compared with the fluorescence excitation and emission of NAD(P)H and riboflavin illustrated in FIG. 5. This data represents material published by Li et al. in *Monitoring Cell Concentration and Activity by Multiple Excitation Fluorometry*, Biotechnol. Prog, 1991, 7:21–27. The present system is designed to illuminate the particles at 325 nm and detect fluorescence in the region from 420 to 560 nm.

Figure 6:
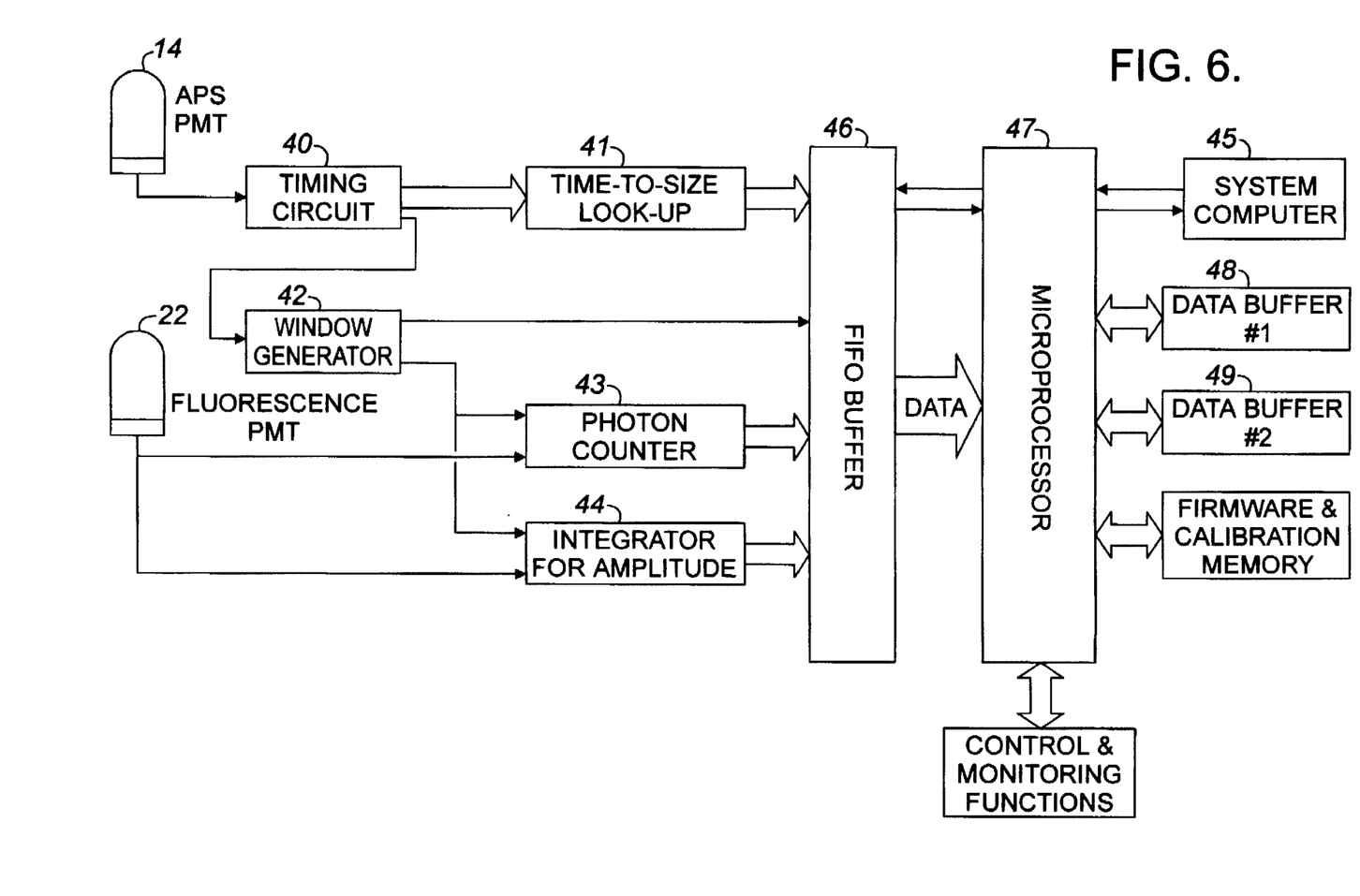
FIG. 6 is a flow diagram of the signal processing for establishing the presence of biologically viable agents using the particle's size, fluorescence intensity and concentration.

As shown in FIG. 6, system electronics measure the time-of-flight (corresponding to particle size) data from the APS PMT signal and the amplitude data of the fluorescence PMT signal for each detected particle.

The APS PMT 14 is triggered by particle interrupting the first laser beam 10. Timing circuit 40 measures the elapsed time to a subsequent APS PMT interruption, signalling that the particle has reached the second laser beam 11. The elapsed time is fed into a look-up table 41 to establish the particle size.

If the elapsed time is valid, window generator 42 opens a short time window of approximately one microsecond (see FIG. 7), signalling the system to begin accepting signals from the fluorescent PMT 24, should any be forthcoming. As the UV laser beam 22 is located slightly further from the nozzle than are the APS beams 10,11, any valid fluorescence signals appear within this time window. This also permits any fluorescence information to be properly associated with the detected particle.

For very faint fluorescent signals (such as that obtained from spores), the fluorescent PMT signal typically consists of only one or two photon pulses, while higher level fluorescence (from clusters of bacteria) gives an analog signal that is the composite of many photons. To ensure the maximum sensitivity and dynamic range, the system electronics measure the intensity of the fluorescence signal in two ways during the time window.

The window generator 42 initiates both a photon pulse counter 43 and a fluorescence integrator circuit 44 for quantification of any fluorescent PMT signal that may occur during the time window.

Photon counting is useful for low levels with less than about 4 photon counts. In this regime photon counting is more selective in rejecting noise in the analog signal and distinguishing between the presence and absence of a fluorescent signal. Also, by performing active signal measurement only during the triggered time window, the system's ability to reject low level background noise is improved.

Particle size, photon pulse counting and fluorescence amplitude data are accumulated for RS-232 serial transmission to a personal computer 45. When each of particle size and corresponding fluorescence measurement are acquired, they are passed to a first-in first-out (FIFO) data buffer 46. The FIFO buffer 46 allows the system to handle bursts of high particle concentration at data rates significantly faster than microprocessor 47 can sort it. Microprocessor 47 reads data from the FIFO buffer 46, sorts and accumulates the data into one of two memory banks 48,49. While data is being accumulated into one memory bank 48, data from the other bank 49 can be transmitted to the personal computer 45. This allows for uninterrupted data acquisition while data is periodically sent to a personal computer for display (re-displayed once every 3 sec) and permanent storage. In addition, the microprocessor 47 performs control and monitoring functions for the fluorescent PMT gain, the UV laser status, the photon counting threshold, the background noise levels, and the system temperature.

Figure 7:
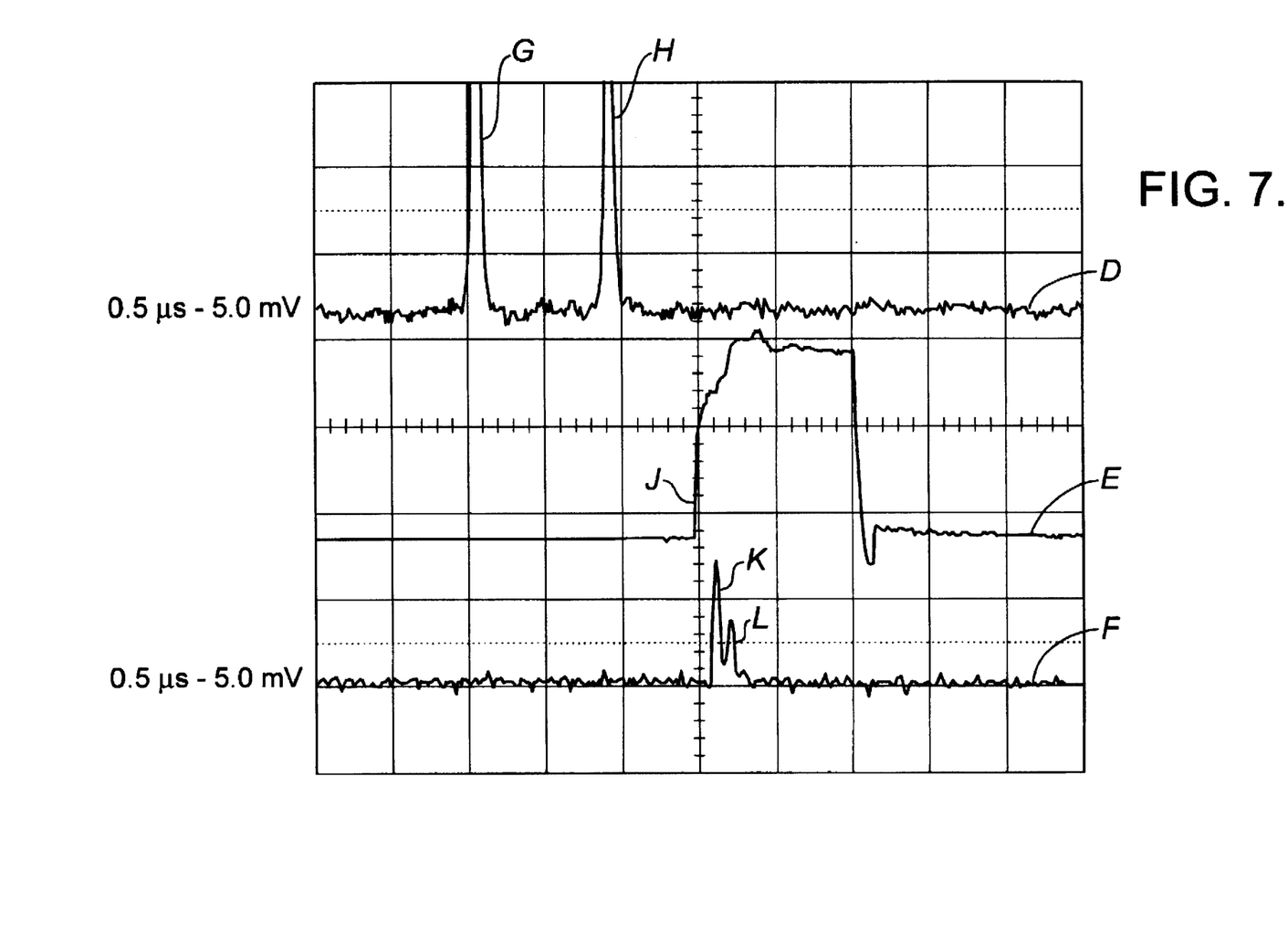
FIG. 7 is a graph illustrating three oscilloscope traces which depict the detection of a particle passing both APS laser beams, the opening of a window for accepting fluorescence emission, and the detection of fluorescence for the particle.

FIG. 7 illustrates three typical oscilloscope traces illustrating an analog signal from the APS PMT (trace D), a window generator timing signal for fluorescence detection (trace E), and an analog fluorescence PMT signal (trace F). Trace D demonstrates the sequential detection of a particle 7 passing each of the APS laser beams 10,11, depicted by peaks G and H respectively. The elapsed time between peaks is correlated with the particles size according to the criteria from the look-up table 41. Step-change J of trace E illustrates the duration of the timing window and peaks K, L illustrate detection of fluorescence from a particle captured.

EXAMPLE I

Testing of the system optics for sensitivity to bacillus subtillis ("BG") bacterial spores was performed with an earlier prototype apparatus which used a low power 10 mW, 354 nm He—Cad laser. The signals from the APS and fluorescent PMT's were sent directly to a digital oscilloscope for viewing. The BG spores were dispersed with a medical nebulizer (Hudson Sales, Temecula, Calif.) and passed through a cylindrical drying tube approximately 45 cm long by 10 cm in diameter. The 5 lpm flow from the nebulizer was mixed with 10 to 20 lpm of clean, dry dilution air in the drying tube. Fluorescence detection consisted of manually triggering the oscilloscope from the APS timing signal and then inspecting the corresponding single sweep of the fluorescence PMT signal. For each trigger, a recording was made of whether or not a pulse representing fluorescence was present in a time window that was defined in relation to the APS PMT signal. This process was repeated a number of times for each data set to determine the percentage of fluorescent signals. No significant fluorescent signals were noted for particles with a time of flight less than approximately 1.0 ns, which corresponds to a particle of 0.7–1.0 μm or smaller. Since individual BG spores have an aerodynamic size of approximately 0.9 μm, they were included in this range and constituted most of the oscilloscope triggers.

When the oscilloscope trigger threshold was raised so that small particles were ignored, it was possible to get a statistically useful number of triggers from only the larger particles having a longer time of flight. It is believed that these larger particles represent clumps of BG spores. For particles with a time of flight corresponding to the size range 1.9 to 4.2 μm, 25 percent produced a fluorescence signal; and 40 percent of particles larger that 2.9 μm produced fluorescence. This initial result provided sufficient proof of the concept to proceed with higher power laser testing.

EXAMPLE II

Figure 8:
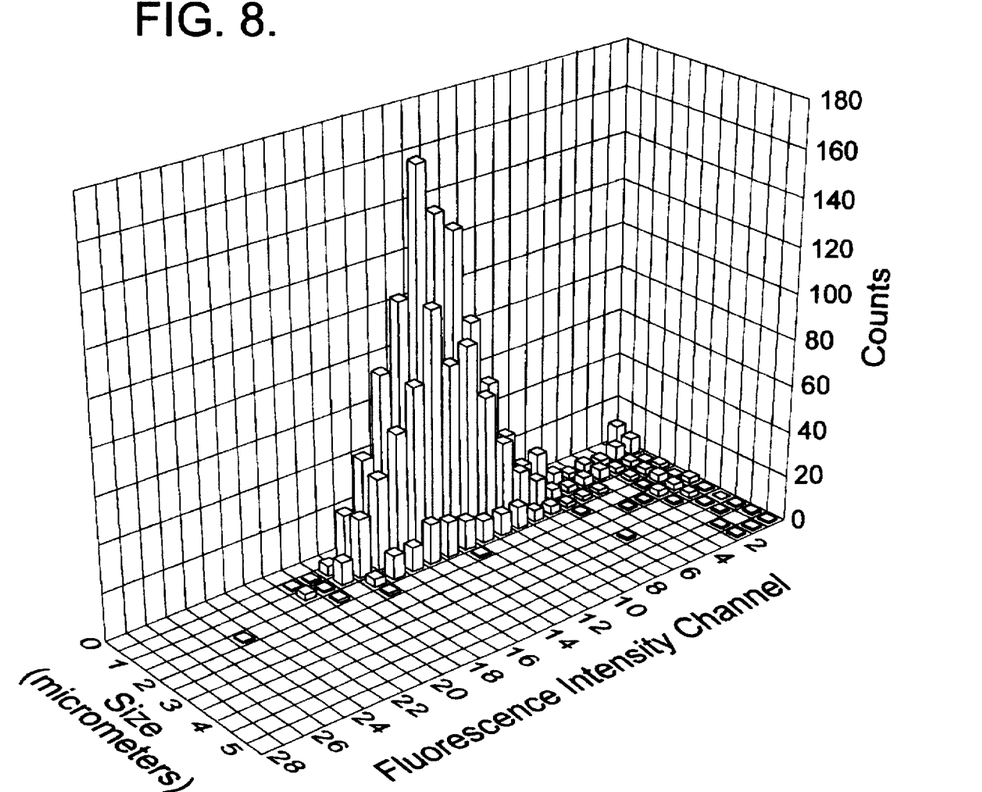
FIG. 8 illustrates size and fluorescence intensity measurements for 1 μm fluorescent-dyed latex beads, tested in Example II.
Figure 9:
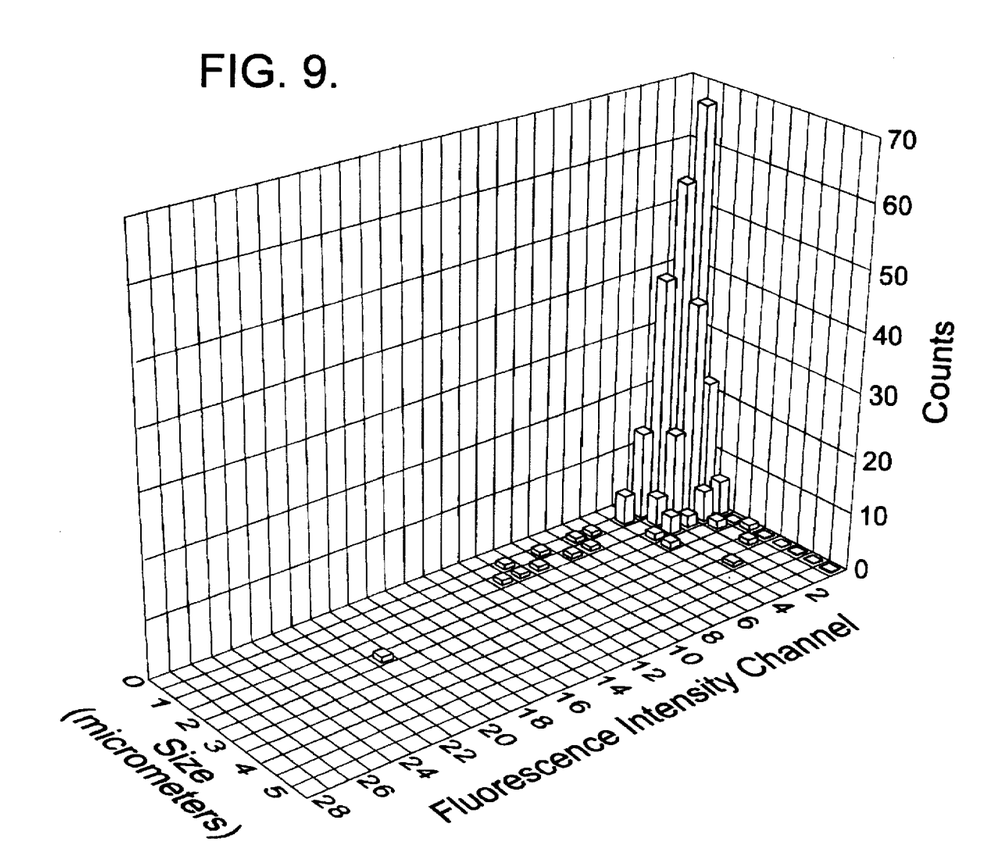
FIG. 9 illustrates the baseline reference plot for the fluorescence measurements for 1 μm polystyrene latex beads without fluorescence dye, tested in Example II.

Initial characterization of the higher power (30 mW) unit was performed using 0.49, 1.0, 1.8 μm polystyrene latex beads treated with a cascade blue dye (from Molecular Probes, Inc., Eugene, Oreg.) that has fluorescent characteristics similar to NADH. FIG. 8 shows size and fluorescence intensity measurements from testing on the 1.0 µm polystyrene latex fluorescent-dyed beads. FIG. 9 shows the corresponding reference plot for measurements of 1.0 µm latex beads without fluorescence dye. The percentage of particles detected as fluorescent is indicated on each plot.

The fluorescence intensity distributions were fairly broad even though the particles are believed to be uniform. The broadness is primarily due to the statistical gain variation of the fluorescent PMT, and also to the non-circularity of the ultraviolet beam profile. Whenever a fluorescent PMT was presented with signals from a small number of photons reaching their photocathode, as in this case, the output pulse amplitudes reflected the variations in gain each photon signal receives in its passage through the PMT gain path. Further, the multimode beam from the UV He—Cad laser could have had intensity variations of about ±15% across the stream of particles.

The non-fluorescent particle measurements showed a background of fluorescence when no actual fluorescence is expected. This is mainly due to residual light passing through the receiving filters and reaching the fluorescence PMT. The red He—Ne beam and the UV He—Cad beam are aligned very close to the nozzle, so that some light inevitably scatters from the nozzle into the receiving optics. This measured background can be subtracted from particle fluorescence measurements. In addition to background light, there is some UV light scattered from the non-fluorescent particles that can produce a fluorescence-like signal. If one assumes a size-dependent amount of UV scattering for particles it is possible to subtract this scattering based signal as well. However, the particle scattering background is significantly smaller than the background signal due to ambient stray light, and to date it has not been treated separately in the data reduction.

Initial attempts to measure BG spore fluorescent showed no distinguishable difference from measurements of ordinary latex beads of a similar size. Thus it was necessary to subtract the amount of fluorescence measurements due to the background light. Secondly, the BG spore concentration in the nebulizer was increased and the aerosol was further diluted using a wind tunnel at the DRES Facility that is designed for bioaerosols.

Having reference to Table 1, fluorescence intensity data and corresponding photon counts data is shown which was obtained from BG spores nebulized into the wind tunnel. Both data sets have had background light subtracted from the data. The percentage of fluorescent spores detected, 16.7 percent for intensity measurements and 3.9 percent for photon counting.

TABLE 1

| Particle | | Percent of Size with fluorescence | |
|---|---|---|---|
| Size Channels (µm) | Percent of Total Counts by Size | Fluorescence Intensity Measure | Photon Counting Measure |
| <0.5 | 1.5 | 14.7 | 0.2 |
| 0.5–1.0 | 53.5 | 14.0 | 1.6 |
| 1.0–1.5 | 32.0 | 15.7 | 3.6 |
| 1.5–2.0 | 7.0 | 25.1 | 12.7 |
| 2.0–2.5 | 2.5 | 35.2 | 23.5 |
| 2.5–3.0 | 0.9 | 43.4 | 28.3 |
| 3.0–3.5 | 0.4 | 43.4 | 22.6 |
| 3.5–4.0 | 0.3 | 29.8 | 8.7 |
| 4.0–4.5 | 0.2 | 32.3 | 3.9 |
| 4.5–5.0 | 0.2 | 27.7 | 0.7 |

TABLE 1-continued

| Particle | | Percent of Size with fluorescence | |
|---|---|---|---|
| Size Channels (µm) | Percent of Total Counts by Size | Fluorescence Intensity Measure | Photon Counting Measure |
| 5.0> | 1.5 | 35.2 | 3.0 |
| Out of 73,024 total particles, for all Sizes | | 16.7 | 3.9 |

For comparison, Table 2 shows data taken in the same session for 1.0 µm non-fluorescent latex beads dispersed from a commercial atomizer and drying system (TSI "Trijet" system). Using the same background light subtraction, fluorescence readings of the latex bead controls were 3.4 percent for intensity measurements and 0.3 percent for photon counts.

TABLE 2

| Particle | | Percent of Size with fluorescence | |
|---|---|---|---|
| Size Channels (µm) | Percent of Total Counts by Size | Fluorescence Intensity Measure | Photon Counting Measure |
| <0.5 | 0.4 | 42.3 | 0.0 |
| 0.5–1.0 | 1.7 | 7.9 | 3.3 |
| 1.0–1.5 | 93.9 | 2.0 | 0.2 |
| 1.5–2.0 | 1.0 | 5.4 | 0.0 |
| 2.0–2.5 | 0.7 | 52.4 | 6.4 |
| 2.5–3.0 | 0.4 | 16.7 | 5.5 |
| 3.0–3.5 | 0.4 | 50.7 | 5.8 |
| 3.5–4.0 | 0.2 | 24.2 | 0.0 |
| 4.0–4.5 | 0.2 | 58.0 | 0.0 |
| 4.5–5.0 | 0.1 | 36.3 | 0.0 |
| 5.0> | 1.0 | 42.6 | 3.5 |
| Out of 5,492 total particles, for all Sizes | | 3.4 | 0.3 |

Further, initial tests with nebulized BG spores showed that overall testing results showing only 5 to 15 percent of BG spore particles producing a fluorescence signal was reasonably consistent with previous study by Ho and Fisher in the memorandum, *Detection of BW Agents: Flow Cytometry Measurement of Bacillus Subtilis (BG) Spore Fluorescence*, 1993, Suffield Memorandum No. 1421, which showed about 12% viability for BG spores in a sonicated solution. It is believed that the action of the nebulizer disassociated spore clumps in a way similar to sonication.

EXAMPLE III

Field trials of the invention were performed at a military testing base.

Figure 10:
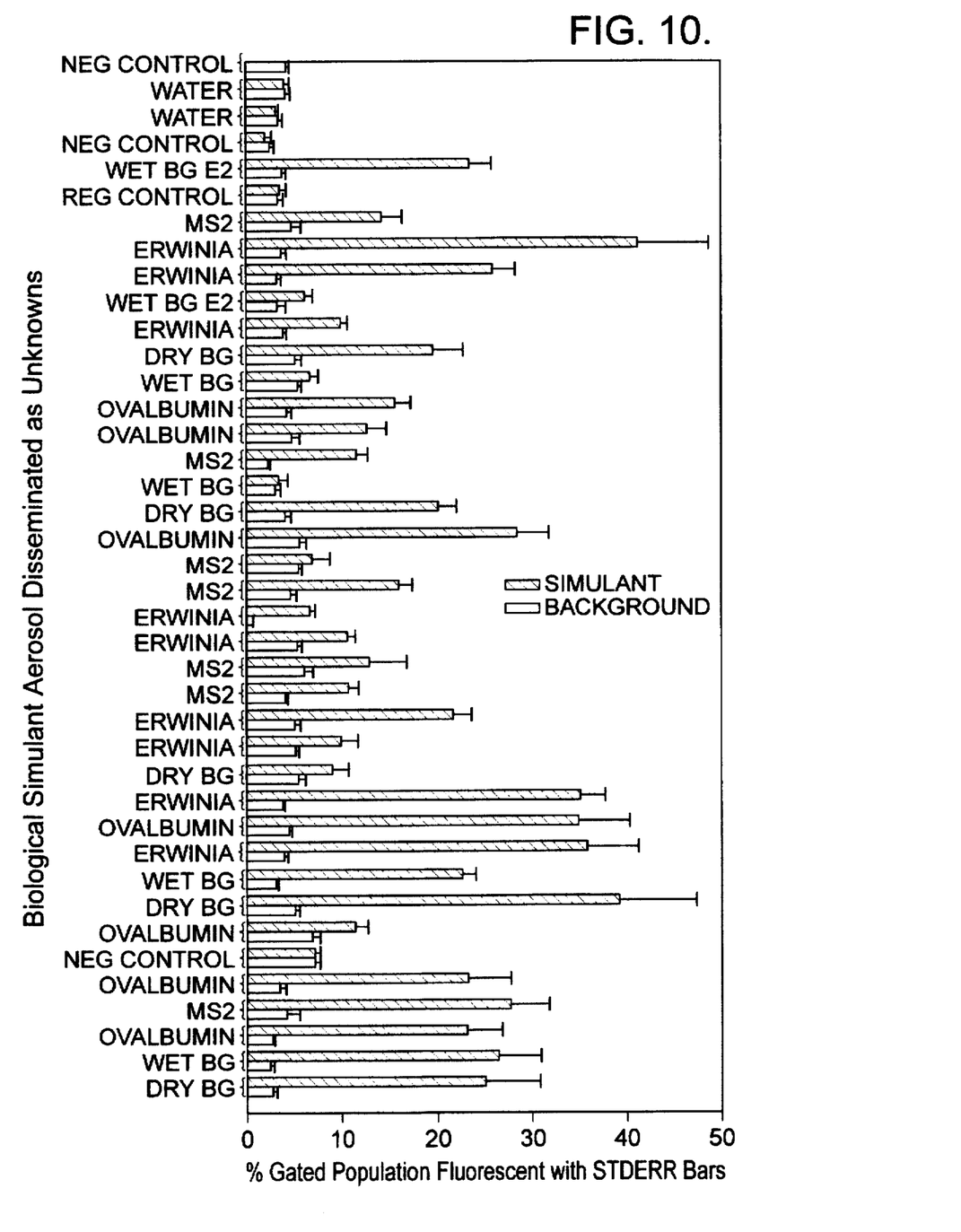
FIG. 10 illustrates background and fluorescence results for a 40 sample blind test of the system.

FIG. 10 illustrates the results of forty tests performed using controls and simulated biological aerosols. The tests were performed outdoors, subjected to the wind and other vagaries of nature. A test typically lasted ½ to 1 hour. The apparatus sampled the ambient air. Neither the testing personnel or the apparatus were advised of the exact nature of the test sample or whether a sample was released at all.

The results are presented on a percentage of gated population basis. A gated population is a representation which masks out any background particles of <2.5 µm and particles with a fluorescence below a threshold brightness. Typically, for every 1000 particles processed through the invention, 900 were masked out and only 100 remained as the gated population.

Prior to each test, a background fluorescence population was determined, shown in FIG. 10 as a hollow bars. Typically the background fluorescence was about 4 to 5% of the gated population.

Control tests were performed to test the susceptibility of the system to reporting false results. The control tests comprised the release of either atomized water (Water) or no simulant at all (Neg. Control). The biological testing simulants included: MS2 (a viral simulant); Erwinia (a vegetative cell bacteria); Ovalbumin (protein-based toxin simulant); and bacillus subtilis spores in dry (Dry BG) and wet (Wet BG) forms.

The apparatus of the invention sampled the ambient airstream on a continuous basis. The shaded bars represent the concentration of particles detected and characterized as biological simulant. The error bars represent natural variation in the fluorescent concentration in the sampled population over the test period.

FIG. 10 illustrates that 39 of 40 tests successfully distinguished between control and simulant "biological events". Only one test did not and that was one subject to a mechanical failure on a control test.

It is apparent that in alternate embodiments of the invention, the size and power consumption associated with the apparatus can be markedly improved by conversion of the He—Cad laser to a solid state ultraviolet laser configured to provide both time-of-flight and fluorescence measurements, reducing the numbers of lasers required to only one.

The embodiments of the invention in which an exclusive property or privilege is claimed are defined as follows:

1. Apparatus for identifying the existence of viable biological particles within an airstream containing a mixture of biologically viable end biologically inert particles, comprising:

means for directing the particles individually and sequentially along a substantially linear path through air;

a source emitting an ultraviolet laser beam directed to contact each particle moving along its linear path in the air, said beam having a wavelength operative to excite biomolecules contained therein to produce fluorescence;

means for measuring the intensity of the fluorescence emitted from each particle and producing a signal indicative thereof; and means for comparing each particle's fluorescence intensity signal against pre-determined criteria and establishing whether that particle is a biologically viable particle or an inert particle.

2. Apparatus as recited in claim 1 wherein the ultraviolet laser beam has a wavelength between 320 and 360 nm and the means for measuring the intensity of the fluorescence emitted is operative to measure it in the wavelength range of 400–540 nm.

3. Apparatus as recited in claim 1 wherein the ultraviolet laser beam has a wavelength operative to excite nicotinamide adenine dinucleotide hydrogen to produce fluorescence therefrom.

4. Apparatus as recited in claim 3 further comprising:

means for measuring the size of each particle and producing a signal indicative thereof;

means for storing the fluorescence intensity signal and the corresponding particle size signal for each particle;

means for counting the number of particles and producing and storing signals indicative thereof; and means for processing the stored fluorescence intensity, particle size and particle count signals and establishing the concentration of biologically viable particles as a function of particle size.

5. Apparatus as recited in claim 4 wherein the means for measuring the size of each particle comprises:

an air discharge nozzle capable of accelerating the flow of the particle-containing airstream through the nozzle so that the particles exit the nozzle individually and sequentially along a substantially linear path, the air flow acting to accelerate a particle passing through the nozzle due to the aerodynamic drag acting thereon, said particle resisting the acceleration by its inertia, whereby the velocity of the particle exiting the nozzle is less than that of the airstream;

means for measuring the velocity of the airstream and producing a signal indicative thereof;

means for emitting two spaced apart laser beams, both of which intersect the particle's linear path, the first beam intersecting the path adjacent the nozzle, the second beam being spaced a known distance downstream;

means for measuring the time taken for the particle to move between the first and second laser beams and producing a signal indicative thereof; and means for processing the known distance between the first and second laser beams and the time signal so as to establish the velocity of the particle and producing a signal indicative thereof; and means for processing the difference between the particle velocity signal and the airstream velocity signal so as to establish the size of the particle.

6. Apparatus as recited in claim 5 wherein the means for emitting two spaced apart laser beams comprises:

the source emitting the ultraviolet laser beam; end means for splitting the ultraviolet laser beam into two beams.

7. A process for detecting the existence of viable biological particles within a stream of air containing a mixture of biologically viable and biologically inert particles, comprising the steps of:

(a) continuously processing the stream of air so as to direct the particles along a substantially linear path through air in a sequential manner;

(b) contacting each particle with an ultraviolet laser beam having a wavelength suitable to excite biomolecules contained therein and produce fluorescence;

(c) detecting fluorescence from the particle and establishing its intensity;

(d) comparing the intensity of each particle's fluorescence against pre-determined criteria so as to establishing whether that particle is biologically viable or is inert; and (e) repeating steps (b)–(d) for sequentially following particles.

8. The process as set forth in claim 7 further comprising:

measuring the size of each particle;

associating the fluorescence intensity of the particle with the size for that particle;

storing the size and fluorescence intensity for the particle and repeating the process for the next particle in sequence;

identifying the size range of particles which are respirable; and establishing the concentration of biologically viable particles which are found to be within the respirable range using the stored particles' sizes and fluorescence intensities.

9. The process as recited in claim 8 comprising:

initially performing the entire process on an ambient stream of air for establishing a background concentration of viable biological particles which appear in the respirable size range;

performing the process for a sample stream of air for establishing the sample's concentration of viable biological particles which appear in the respirable size range; and comparing the background and sample concentrations of biologically viable particles for identifying sample concentrations higher than the background concentrations.

10. The process as set forth in claim 9 wherein the process steps are all conducted sufficiently quickly so as to maintain continuous processing of the sample stream of particle-containing air.

11. The process as recited in claim 10, wherein size and fluorescence intensity signals produced for particles having a size smaller than a threshold size and particles emitting fluorescence at an intensity lower than a threshold fluorescence intensity are suppressed from the background and sample concentrations so as to better distinguish the viable biological particles from the inert particles.

12. The process as recited in claim 9, wherein size and fluorescence intensity signals produced for particles having a size smaller than a threshold size and particles emitting fluorescence at an intensity lower than a threshold fluorescence intensity are suppressed from the background and sample concentrations so as to better distinguish the viable biological particles from the inert particles.

13. The process as recited in claim 8 wherein the stream of air is continuously processed by:

rapidly accelerating the stream of air containing particles to a known velocity wherein each particle accelerates to reach a characteristic velocity, slower than the velocity of the stream of air itself, so that, as a function of the particle's inertia and aerodynamic properties, each particle becomes separated from the others and becomes distributed substantially sequentially along a linear path through the air;

directing each particle to intersect two laser beams of known spacing;

measuring the particle's transit time between the two laser beams;

establishing measures of the particle's velocity from the particle's transit time and the laser beam spacing; and comparing the relative velocities of the particle and stream of air so as to establish the size of the particle.

14. The process as recited in claim 13 wherein the ultraviolet laser beam has a wavelength operative to excite nicotinamide adenine dinucleotide hydrogen to produce fluorescence therefrom.

15. The process as recited in claim 13 wherein the ultraviolet laser beam has a wavelength between 320 and 360 nm and the means for measuring the intensity of the fluorescence emitted is operative to measure in the wavelength range of 400–540 nm.

16. The process as set forth in claim 8 wherein the ultraviolet laser beam has a wavelength operative to excite nicotinamide adenine dinucleotide hydrogen to produce fluorescence therefrom.

17. The process as set forth in claim 8 wherein the ultraviolet laser beam has a wavelength between 320 and 360 nm and the means for measuring the intensity of the fluorescence emitted is operative to measure it in the wavelength range of 400–540 nm.

18. The process as recited in claim 7 wherein the stream of air is continuously processed by:

rapidly accelerating the stream of air containing particles to a known velocity wherein each particle accelerates to reach a characteristic velocity, slower than the velocity of the stream of air itself, so that, as a function of the particle's inertia and aerodynamic properties, each particle becomes separated from the others and becomes distributed substantially sequentially along a linear path through the air.

19. The process as set forth in claim 18 wherein the ultraviolet laser beam has a wavelength operative to excite nicotinamide dinucleotide hydrogen to produce fluorescence therefrom.

20. The process as recited in claim 18 wherein the ultraviolet laser beam has a wavelength between 320 and 360 nm and the means for measuring the intensity of the fluorescence emitted is operative to measure it in the wavelength range of 400–540 nm.

21. The process as recited in claim 7 wherein the ultraviolet laser beam has a wavelength operative to excite nicotinamide adenine dinucleotide hydrogen to produce fluorescence therefrom.

22. The process as recited in claim 7 wherein the ultraviolet laser beam has a wavelength between 320 and 360 nm and the means for measuring the intensity of the fluorescence emitted is operative to measure it in the wavelength range of 400–540 nm.

* * * * *